(12) United States Patent
Johnson et al.

(10) Patent No.: US 9,307,996 B2
(45) Date of Patent: Apr. 12, 2016

(54) DETACHMENT ACTUATOR FOR USE WITH MEDICAL DEVICE DEPLOYMENT SYSTEMS

(75) Inventors: Kirk L. Johnson, Weston, FL (US);
Juan A. Lorenzo, Davie, FL (US);
Robert Lulo, Pembroke Pines, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1036 days.

(21) Appl. No.: 12/085,885

(22) PCT Filed: Dec. 12, 2006

(86) PCT No.: PCT/US2006/061929
§ 371 (c)(1),
(2), (4) Date: Jun. 2, 2008

(87) PCT Pub. No.: WO2007/070797
PCT Pub. Date: Jun. 21, 2007

(65) Prior Publication Data
US 2009/0270877 A1    Oct. 29, 2009

Related U.S. Application Data

(60) Provisional application No. 60/749,879, filed on Dec. 13, 2005.

(51) Int. Cl.
| | |
|---|---|
| *A61F 2/06* | (2013.01) |
| *A61B 17/12* | (2006.01) |
| *A61F 2/95* | (2013.01) |
| *A61B 17/00* | (2006.01) |

(52) U.S. Cl.
CPC ....... *A61B 17/12022* (2013.01); *A61B 17/1214* (2013.01); *A61F 2/95* (2013.01); *A61B 2017/0046* (2013.01); *A61B 2017/12054* (2013.01); *A61F 2002/9505* (2013.01); *A61F 2002/9511* (2013.01)

(58) Field of Classification Search
CPC ............... A61B 2017/1205; A61B 17/12022; A61B 17/1214; A61B 2017/0046; A61F 2/95; A61F 2002/9517
USPC .......................... 606/167–185, 107; 623/6.12
See application file for complete search history.

(56) References Cited

U.S. PATENT DOCUMENTS

| | | | |
|---|---|---|---|
| 1,294,284 | A | 2/1919 | Logeman |
| 2,549,731 | A | 4/1951 | Wattley |

(Continued)

FOREIGN PATENT DOCUMENTS

| | | |
|---|---|---|
| EP | 754435 A1 | 1/1997 |
| EP | 832607 A1 | 4/1998 |

(Continued)

OTHER PUBLICATIONS

European Supplemental Search Report EP06846571.5 dated Oct. 6, 2010.

*Primary Examiner* — Katrina Stransky (57) ABSTRACT

A detachment actuator for use with an implantable medical device deployment system that guide and deploys the medical device at a target location within a body vessel. The detachment actuator includes a first portion that is connected the implantable medical device and a second portion that is attached to a control member the controls the release of the medical device, The second portion of the detachment actuator detaches and moves away from the first portion of the detachment actuator to move the control member and release the medical device.

25 Claims, 3 Drawing Sheets

(56) References Cited

U.S. PATENT DOCUMENTS

| | | | |
|---|---|---|---|
| 2,638,365 | A | 5/1953 | Jones |
| 3,429,408 | A | 2/1969 | Maker |
| 3,547,103 | A | 12/1970 | Cook |
| 3,963,322 | A | 6/1976 | Gryctko |
| 4,655,219 | A | 4/1987 | Petruzzi |
| 4,830,002 | A | 5/1989 | Semm |
| 5,108,407 | A | 4/1992 | Geremia |
| 5,109,867 | A | 5/1992 | Twyford, Jr. |
| 5,117,838 | A | 6/1992 | Palmer |
| 5,122,136 | A | 6/1992 | Guglielmi |
| 5,156,430 | A | 10/1992 | Mori |
| 5,217,438 | A | 6/1993 | Davis |
| 5,217,484 | A | 6/1993 | Marks |
| 5,234,437 | A | 8/1993 | Sepetka |
| 5,250,071 | A | 10/1993 | Palermo |
| 5,261,916 | A | 11/1993 | Engelson |
| 5,263,964 | A * | 11/1993 | Purdy ............................ 606/200 |
| 5,304,195 | A | 4/1994 | Twyford, Jr. |
| 5,334,210 | A | 8/1994 | Gianturco |
| 5,350,397 | A | 9/1994 | Palermo |
| 5,354,295 | A | 10/1994 | Guglielmi |
| 5,381,788 | A * | 1/1995 | Matula et al. ................. 600/214 |
| 5,382,259 | A | 1/1995 | Phelps |
| 5,397,304 | A | 3/1995 | Truckai |
| 5,417,708 | A | 5/1995 | Hall |
| 5,427,118 | A | 6/1995 | Nita |
| 5,540,680 | A | 7/1996 | Guglielmi |
| 5,571,089 | A | 11/1996 | Crocker |
| 5,582,619 | A | 12/1996 | Ken |
| 5,601,600 | A | 2/1997 | Ton |
| 5,624,449 | A | 4/1997 | Pham |
| 5,725,546 | A | 3/1998 | Samson |
| 5,725,549 | A | 3/1998 | Lam |
| 5,746,769 | A | 5/1998 | Ton |
| 5,749,894 | A | 5/1998 | Engelson |
| 5,765,449 | A | 6/1998 | LeMire |
| 5,782,747 | A | 7/1998 | Zimmon |
| 5,800,455 | A | 9/1998 | Palermo |
| 5,853,418 | A | 12/1998 | Ken |
| 5,895,391 | A | 4/1999 | Farnholtz |
| 5,895,411 | A | 4/1999 | Irie |
| 5,910,144 | A | 6/1999 | Hayashi |
| 5,925,059 | A | 7/1999 | Palermo |
| 5,989,242 | A | 11/1999 | Saadat |
| 6,107,004 | A | 8/2000 | Donadio, III |
| 6,113,622 | A | 9/2000 | Hieshima |
| 6,190,373 | B1 | 2/2001 | Palermo |
| 6,193,728 | B1 | 2/2001 | Ken |
| RE37,117 | E | 3/2001 | Palermo |
| 6,203,547 | B1 | 3/2001 | Nguyen |
| 6,217,566 | B1 | 4/2001 | Ju |
| 6,231,597 | B1 * | 5/2001 | Deem et al. ................... 623/1.12 |
| 6,238,415 | B1 | 5/2001 | Sepetka |
| 6,277,125 | B1 | 8/2001 | Barry |
| 6,280,464 | B1 | 8/2001 | Hayashi |
| 6,296,622 | B1 | 10/2001 | Kurz |
| 6,338,736 | B1 | 1/2002 | Boosfeld |
| 6,346,091 | B1 | 2/2002 | Jacobsen |
| 6,361,547 | B1 | 3/2002 | Hieshima |
| 6,371,953 | B1 | 4/2002 | Beyar |
| 6,451,025 | B1 | 9/2002 | Jervis |
| 6,451,026 | B1 | 9/2002 | Biagtan |
| 6,471,713 | B1 * | 10/2002 | Vargas et al. ................. 606/153 |
| 6,478,773 | B1 | 11/2002 | Gandhi |
| 6,488,694 | B1 * | 12/2002 | Lau et al. ...................... 606/194 |
| 6,500,149 | B2 | 12/2002 | Gandhi |
| 6,537,314 | B2 | 3/2003 | Langberg |
| 6,544,225 | B1 | 4/2003 | Lulo |
| 6,554,849 | B1 | 4/2003 | Jones |
| 6,561,988 | B1 | 5/2003 | Turturro |
| 6,562,064 | B1 | 5/2003 | deBeer |
| 6,575,965 | B1 | 6/2003 | Fitch et al. |
| 6,585,718 | B2 | 7/2003 | Hayzelden |
| 6,607,538 | B1 | 8/2003 | Ferrera |
| 6,638,293 | B1 | 10/2003 | Makower |
| 6,660,020 | B2 | 12/2003 | Wallace |
| 6,685,653 | B2 | 2/2004 | Ehr |
| 6,689,141 | B2 | 2/2004 | Ferrera |
| 6,749,560 | B1 | 6/2004 | Konstorum |
| 6,761,733 | B2 | 7/2004 | Chobotov |
| 6,793,673 | B2 | 9/2004 | Kowalsky |
| 6,797,001 | B2 | 9/2004 | Mathis |
| 6,811,561 | B2 | 11/2004 | Diaz |
| 6,835,185 | B2 | 12/2004 | Ramzipoor |
| 6,849,081 | B2 | 2/2005 | Sepetka |
| 6,849,303 | B2 | 2/2005 | Dave |
| 6,902,572 | B2 | 6/2005 | Beulke |
| 6,911,016 | B2 | 6/2005 | Balzum |
| 6,935,058 | B2 | 8/2005 | Sadegh |
| 6,953,472 | B2 | 10/2005 | Palmer |
| 6,958,068 | B2 | 10/2005 | Hieshima |
| 6,966,914 | B2 | 11/2005 | Abe |
| 6,994,711 | B2 | 2/2006 | Hieshima |
| 7,033,374 | B2 | 4/2006 | Schaefer |
| 7,044,134 | B2 | 5/2006 | Khairkhahan |
| 7,201,768 | B2 | 4/2007 | Diaz |
| 7,323,000 | B2 | 1/2008 | Monstdt |
| 7,344,558 | B2 | 3/2008 | Lorenzo |
| 7,367,987 | B2 | 5/2008 | Balgobin |
| 7,371,251 | B2 | 5/2008 | Mitelberg |
| 7,371,252 | B2 | 5/2008 | Balgobin |
| 7,377,932 | B2 | 5/2008 | Mitelberg |
| 7,473,266 | B2 | 1/2009 | Glaser |
| 7,582,101 | B2 | 9/2009 | Jones |
| 7,708,754 | B2 | 5/2010 | Balgobin |
| 7,708,755 | B2 | 5/2010 | Davis, III |
| 7,722,636 | B2 * | 5/2010 | Farnan .......................... 606/200 |
| 8,182,506 | B2 | 5/2012 | Fitz |
| 2001/0002438 | A1 | 5/2001 | Sepetka |
| 2001/0044633 | A1 | 11/2001 | Klint |
| 2002/0022837 | A1 | 2/2002 | Mazzocchi |
| 2002/0082499 | A1 | 6/2002 | Jacobsen |
| 2002/0099408 | A1 | 7/2002 | Marks |
| 2002/0111647 | A1 | 8/2002 | Khairkhahan |
| 2002/0151915 | A1 | 10/2002 | Hieshima |
| 2002/0165569 | A1 | 11/2002 | Ramzipoor |
| 2003/0125709 | A1 | 7/2003 | Eidenschink |
| 2003/0220666 | A1 | 11/2003 | Mirigian |
| 2004/0006363 | A1 | 1/2004 | Schaefer |
| 2004/0034363 | A1 | 2/2004 | Wilson |
| 2004/0044361 | A1 | 3/2004 | Frazier |
| 2004/0059404 | A1 * | 3/2004 | Bjorklund et al. ............ 607/126 |
| 2004/0073230 | A1 | 4/2004 | Mulholland |
| 2004/0111095 | A1 | 6/2004 | Gordon |
| 2004/0127918 | A1 | 7/2004 | Nikolchev |
| 2004/0225299 | A1 * | 11/2004 | Carrison et al. ............... 606/108 |
| 2005/0038470 | A1 | 2/2005 | van der Burg |
| 2005/0043755 | A1 | 2/2005 | Wilson |
| 2005/0113863 | A1 | 5/2005 | Ramzipoor |
| 2005/0113864 | A1 | 5/2005 | Gandhi |
| 2005/0149108 | A1 | 7/2005 | Cox |
| 2005/0165442 | A1 | 7/2005 | Thinnes |
| 2005/0171572 | A1 | 8/2005 | Martinez |
| 2005/0177132 | A1 | 8/2005 | Lentz |
| 2005/0216018 | A1 | 9/2005 | Sennett |
| 2006/0004346 | A1 | 1/2006 | Begg |
| 2006/0100687 | A1 | 5/2006 | Fahey |
| 2006/0116714 | A1 | 6/2006 | Sepetka |
| 2006/0121218 | A1 | 6/2006 | Obara |
| 2006/0189896 | A1 | 8/2006 | Davis |
| 2006/0200047 | A1 | 9/2006 | Galdonik |
| 2006/0276823 | A1 | 12/2006 | Mitelberg |
| 2006/0276824 | A1 | 12/2006 | Mitelberg |
| 2006/0276825 | A1 | 12/2006 | Mitelberg |
| 2006/0276826 | A1 | 12/2006 | Mitelberg |
| 2006/0276827 | A1 | 12/2006 | Mitelberg |
| 2006/0276828 | A1 | 12/2006 | Balgobin |
| 2006/0276829 | A1 | 12/2006 | Balgobin |
| 2006/0276830 | A1 | 12/2006 | Balgobin |
| 2006/0276832 | A1 | 12/2006 | Balgobin |
| 2006/0276833 | A1 | 12/2006 | Balgobin |
| 2006/0276834 | A1 | 12/2006 | Balgobin |
| 2007/0010849 | A1 | 1/2007 | Balgobin |

(56) References Cited

U.S. PATENT DOCUMENTS

2007/0010850 A1 1/2007 Balgobin
2007/0118172 A1 5/2007 Balgobin
2007/0203519 A1 8/2007 Lorenzo
2007/0239191 A1 10/2007 Ramzipoor
2007/0299422 A1 12/2007 Inganas

FOREIGN PATENT DOCUMENTS

| EP | 1537838 A1 | 6/2005 |
|---|---|---|
| WO | WO 9311825 A1 | 6/1993 |
| WO | 9638092 A1 | 12/1996 |
| WO | 2004008974 A1 | 1/2004 |
| WO | WO 2004087006 A2 | 10/2004 |

* cited by examiner

DETACHMENT ACTUATOR FOR USE WITH MEDICAL DEVICE DEPLOYMENT SYSTEMS

This application claims the benefit of U.S. Provisional Patent Application No. 60/749,879, filed Dec. 13, 2005, which is hereby incorporated herein by reference.

FIELD OF THE INVENTION

This invention generally relates to detachment actuators for use with medical device deployment systems that actuate deployment of implantable medical devices at target locations within a human body vessel, and methods of using the same.

DESCRIPTION OF RELATED ART

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat defects of the cranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. An implantable medical device, such as an embolic coil or vascular stent, is attached to the end of a delivery member which pushes the medical device through the catheter and out of the distal end of the catheter into the delivery site. Some of the delivery systems associated with these procedures utilize a control wire, sometimes referred to as a pull wire, to activate the release and deployment of the medical device. For example, U.S. Pat. No. 5,250,071 to Palermo, which is hereby incorporated herein by reference, describes a detachment system whereby interlocking clasps of the system and the coil are held together by a control wire. The control wire is moved proximally to disengage the clasps from each other.

Additionally, U.S. patent application Ser. No. 11/461,245, filed Jul. 31, 2006, to Mitelburg, et al., which is hereby incorporated herein by reference for its disclosure of a distal-portion detachment mechanism with which the present invention can be utilized, describes a detachment system wherein a control wire engages a hook or an eyelet to attach a medical device to the deployment system. The control wire is moved in a proximal direction to disengage it from the hook and release the medical device.

There remains a need for mechanisms or methods that can be used by the medical professional to manipulate the control wire to provide for a quick and timely deployment of the implantable medical device at a target location within a body vessel.

SUMMARY OF THE INVENTION

In accordance with one embodiment or aspect of the present invention, an actuator is provided for use with an implantable medical device deployment system including a control member that controls the release of the implantable medical device upon movement of the control member. The actuator includes a first portion and a second portion. The first portion can be connected to the deployment system, and the second portion can be connected to the control member. The second portion is detachable from the first portion upon the application of torque to either the first portion or the second portion. After the second portion has been detached from the first portion, the second portion can be separated from the first portion to cause movement of the control member to release the medical device.

In accordance with a further embodiment or aspect of the present invention, an actuator is provided for use with an implantable medical device deployment system including a control member that controls the release of the implantable medical device upon movement of the control member. The actuator includes a first portion and a second portion wherein the first portion and the second portion are integral. The first portion can be connected to the deployment system, and the second portion can be connected to the control member. A fracturable member is between the first and second portions, and the second portion is detachable from the first portion by fracturing the fracturable member. After the second portion is detached from the first portion, the second portion can be separated from the first portion to cause movement of the control member to release the medical device.

In accordance with a yet another embodiment or aspect of the present invention, a deployment system is provided for delivering an implantable medical device to a target location of a body vessel. The deployment system includes a generally elongated carrier member having a proximal end portion and a distal end portion, and an implantable medical device releasably attached to the distal end portion of the carrier member. The deployment system also includes a control member whose movement causes the release of the implantable medical device from the distal end portion of the carrier member. Additionally, the deployment system includes an actuator including a first portion and a second portion. The first portion of the actuator is connected to the carrier member, and the second portion of the actuator is connected to the control member. The second portion is detachable from the first portion by applying torque to either the first portion or the second portion of the actuator. The second portion can then be separated by a distance from the first portion to cause movement of the control member relative to the carrier member and release the implantable medical device.

Yet another embodiment or aspect of the present invention is a method of deploying an implantable medical device to a target location of a body vessel. The method includes providing a deployment system having a generally elongated carrier member including a proximal end portion and a distal end portion, and an implantable medical device releasably secured to the distal end portion of the carrier member. The deployment system also has a control member whose movement causes the release of the implantable medical device from the distal end portion of the carrier member. Additionally, the deployment system also includes an actuator having a first portion and a second portion. The first portion of the actuator is connected to the proximal end portion of the carrier member, and the second portion of the actuator is connected to the control member. The method furthering including positioning the implantable medical device generally adjacent to a target location within a body vessel. Detaching the second portion of the actuator from the first portion of the actuator by applying torque to either the first portion or second portion of the actuator, and separating the second portion of the actuator from the first portion of the actuator, thereby causing movement of the control member and release of the medical device.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIGS. 1-4 illustrate an implantable medical device deployment system, generally designated at 10, utilizing one embodiment of a distal end portion deployment system suitable for use with a detachment actuator or mechanism in accordance with the present invention, generally designated at 12. The illustrated deployment system 10 is generally similar to the deployment system disclosed in U.S. patent application Ser. No. 11/461,245, filed Jul. 31, 2006, to Mitelburg et al., which is hereby incorporated herein by reference. However, it will be understood that the detachment actuator of the present invention can be used in conjunction with various types of deployment systems having various configuration, features and attachment and release mechanisms, such as the deployment system disclosed in U.S. Pat. No. 5,250,071, which is hereby incorporated herein by reference.

Figures 1, 2, 3:
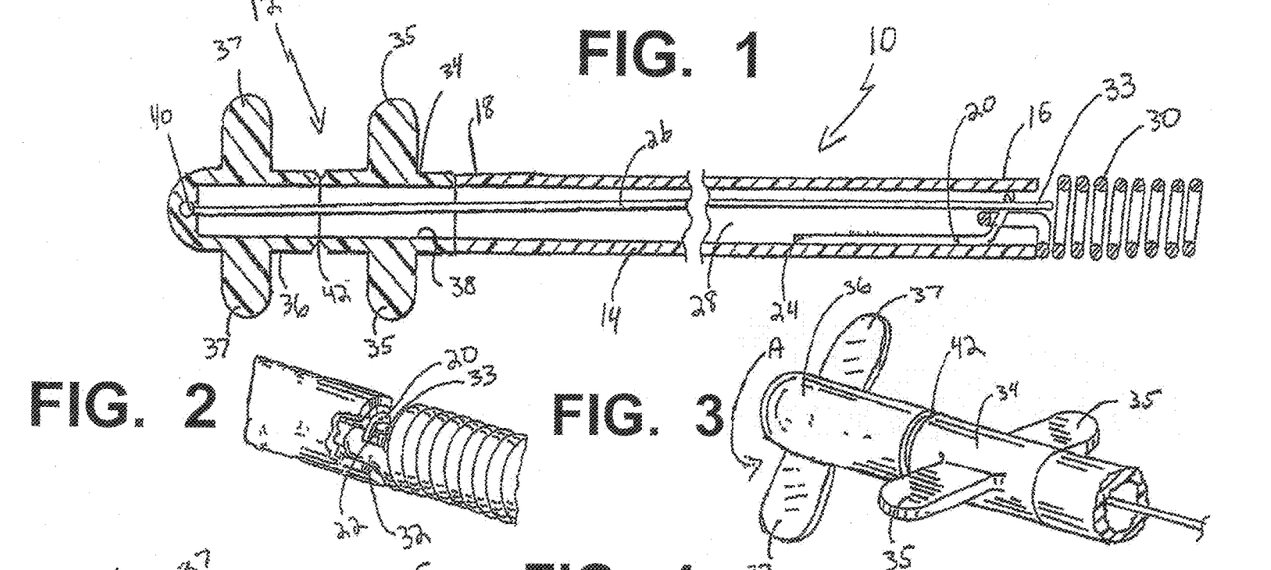
FIG. 1 is a cross-sectional view of a medical device deployment system utilizing one embodiment of a detachment actuator in accordance with the present invention.
FIG. 2 is a front perspective view of a distal end portion of the carrier member of FIG. 1.
FIG. 3 is a perspective view of the detachment actuator of FIG. 1, shown with the first portion rotated relative to the second portion.

The deployment system 10 is comprised of a generally hollow elongated carrier member or pusher 14 having a distal end portion 16 and a proximal end portion 18. Preferably, the carrier member 14 is a hypotube that may be comprised of a biocompatible material, such as stainless steel. The hypotube typically will have a diameter of between about 0.010 inch (0.254 mm) and about 0.015 inch (0.381 mm), a preferred tube having a diameter of approximately 0.013 inch (0.330 mm). Such a carrier member 14 is suitable for delivering and deploying implantable medical devices, such as embolic coils, vascular stents or the like, to target locations, typically aneurysms, within the neurovasculature, but differently sized carrier members comprised of other materials may be useful for different applications.

An engagement member 20 is associated with the distal end portion 16 of the carrier member 14. The engagement member 20 can comprise a distal end length of an elongated wire loosely bent in half to define an opening 22 (FIG. 2). The proximal end or ends 24 of the engagement member 20 can be fixedly connected to the carrier member 14 at a location proximal to the distal end portion 16.

In an alternative embodiment, the engagement member 20 can comprise a flat ribbon defining the opening 22 at a distal portion thereof. In either embodiment, the engagement member 20 is preferably deformable to the up-turned condition illustrated in FIGS. 1, 2, 5 and 7. Additionally, the engagement member 20 is preferably elastically deformable to the up-turned condition of FIGS. 1, 2, 5 and 7, such that it will return to a substantially flat condition, illustrated in FIGS. 4, 6 and 8, when not otherwise constrained, as will be explained in more detail below. The engagement member 20 may be comprised of any of a number of materials, including nitinol and stainless steel. The function of the engagement member 20 will be described in greater detail herein.

The deployment system 10 further includes a control member 26, such as a control wire or pullwire, received within the lumen 28 of the carrier member 14 and movable with respect to the engagement member 20. The control member 26 stretches beyond the proximal end portion 18 of the carrier member 14 and is connected to the detachment actuator 12. The control member 26 may be a wire comprised of any of a number of materials, including nitinol. The function of the control member 26 will be described in greater detail herein.

As shown in FIGS. 1, 2, 5 and 7, an implantable medical device 30, such as the illustrated embolic coil, is releasably attached to the distal end portion 16 of the carrier member 14 by the engagement member 20. However, it will be appreciated that virtually any implantable medical device may be delivered and deployed by the deployment system.

To connect the implantable medical device 30 to the distal end portion 16 of the carrier member 14, an aperture-containing proximal end portion 32 of the implantable medical device 30 is placed adjacent to opening 22 of the engagement member 20, which is then deformed to the up-turned condition of FIGS. 1, 2, 5 and 7. Alternatively, the opening 22 may be moved to the up-turned condition prior to placement of the implantable medical device 30. In the up-turned condition, at least a portion of the opening 22 passes through the aperture of the proximal end portion 32.

Figure 4:
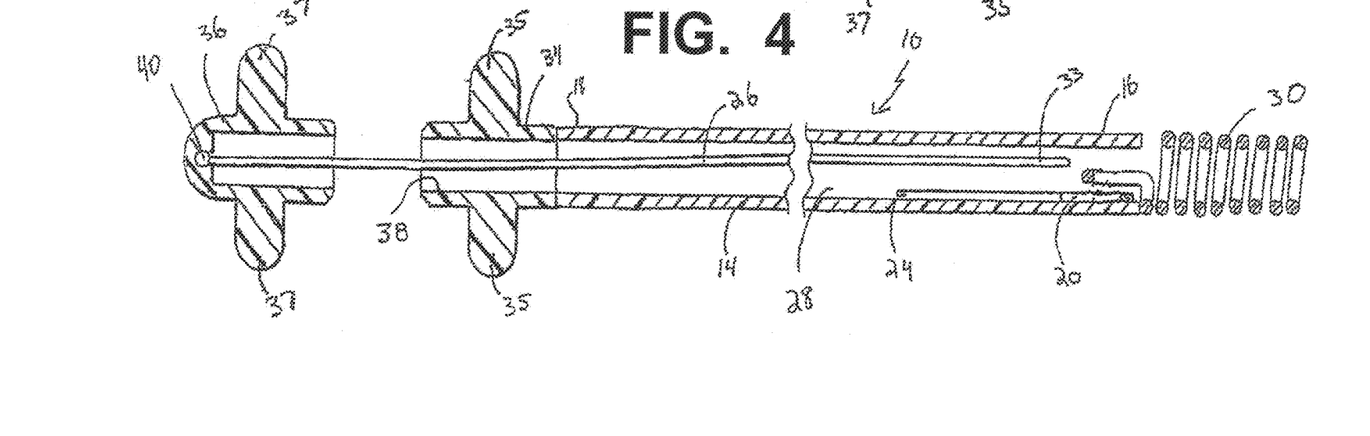
FIG. 4 is a cross-sectional view of the deployment system of FIG. 1, shown in the actuated position to deploy the medical device.
Figure 5:
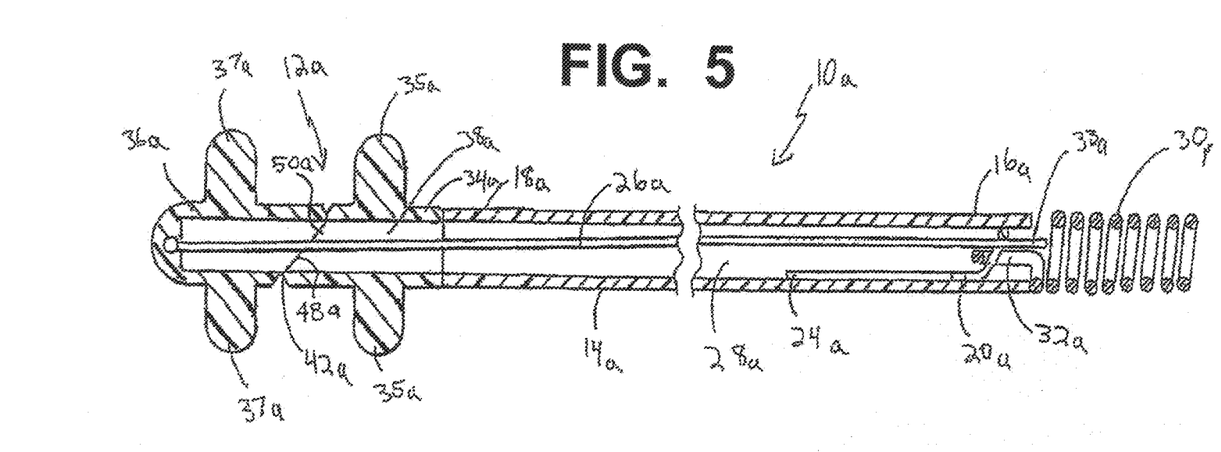
FIG. 5 is a cross-sectional view of a medical device deployment system utilizing another embodiment of a detachment actuator in accordance with the present invention.
Figure 6:
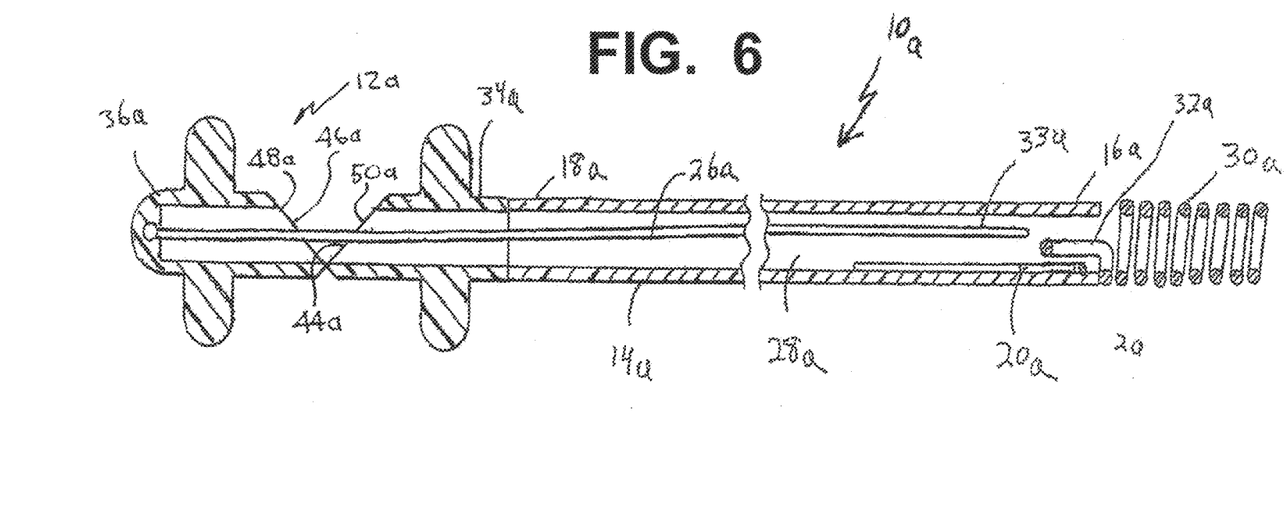
FIG. 6 is a cross-sectional view of the deployment system of FIG. 5 shown in the actuated position to deploy the medical device.
Figure 7:
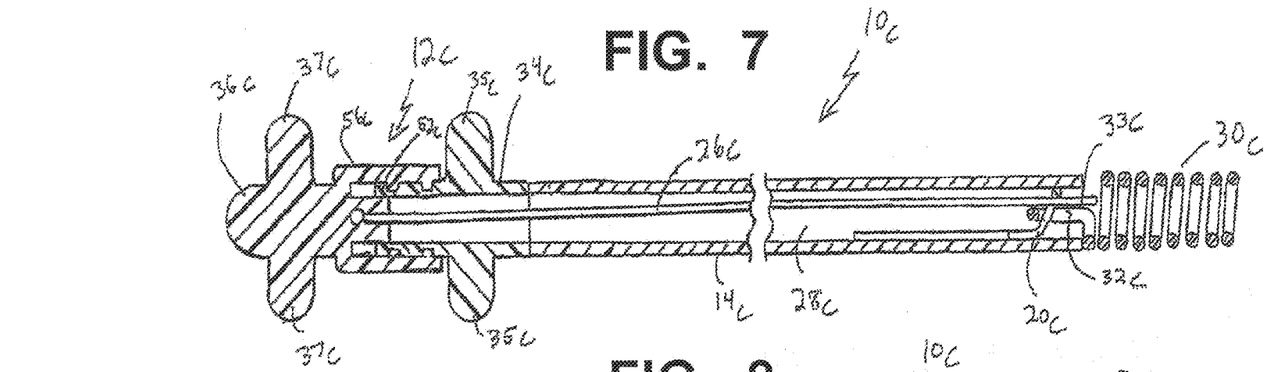
FIG. 7 is a cross-sectional view of a medical device deployment system utilizing yet another embodiment of a detachment actuator in accordance with the present invention.
Figure 8:
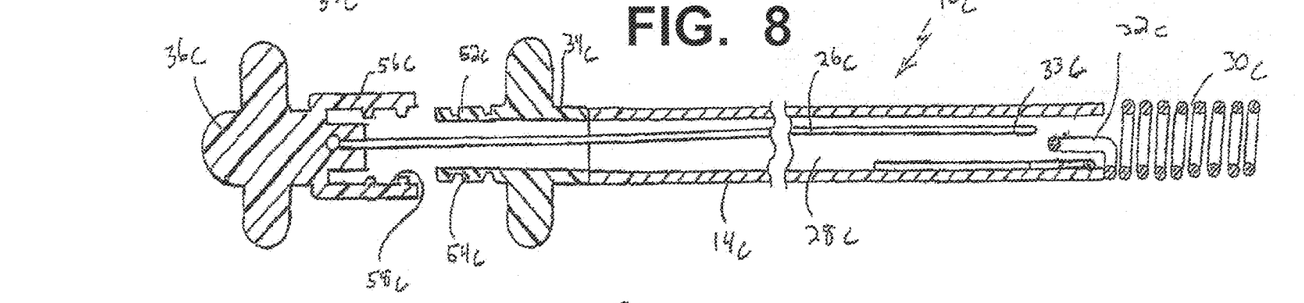
FIG. 8 is a cross-sectional view of the deployment system of FIG. 7, shown in the actuated configuration to deploy the medical device.

As described herein, the engagement member 20 is preferably elastically deformable to the up-turned condition of FIGS. 1, 2, 5 and 7 so it will tend to return to a substantially flat condition as illustrated in FIGS. 4, 6 and 8 In order to prevent this, and to consequently lock the implantable medical device 30 to the engagement member 20, the distal end portion 33 of the control member 26 is moved axially through the opening 22 to the position shown in FIGS. 1, 2, 5 and 7. In this connected condition, the control member 26 holds the engagement member 20 in the up-turned condition, and the engagement member 20 releasably secures the proximal end portion 32 of the implantable medical device 30 to the distal end portion 16 of the carrier member 14.

The detachment actuator 12, which can also be utilized as a percutaneous handle, includes a first or distal end portion 34 and a second or proximal end portion 36. Preferably, the detachment actuator 12 is generally cylindrical in shape. However, the general overall shape of detachment actuator could be any number of shapes. The first portion 34 can include a first set of wings 35, and the second portion 36 can include a second set of wings 37. The wings 35, 37 can provide gripping surfaces so that a user can easily grasp the detachment actuator 12 and manipulate it by hand. If desired, the wings 35, 37 can also aid in attaching the detachment actuator 12 to the skin of a patient by providing a surface area in which tape can be readily applied to the detachment actuator. When the wings 35, 37 are against the skin of a patient the wings aid in preventing undesired premature rotation between the first and second portions 34, 36 of the detachment actuator 12.

The first portion 34 of the detachment actuator 12 is attached to the proximal end portion 18 of the carrier member 14 by adhesive, weld or mechanical connection. Alternatively, the first portion 34 can be integral with the proximal end portion 18 of the carrier member 14. Preferably, the first portion 34 includes a lumen 38 that allows the control member 26 to pass therethrough so that the proximal end portion 40 of the control member 26 can be connected to the second portion 36 of the detachment actuator 12. The proximal end portion 40 of the control member 26 can be connected to the second portion 36 of the detachment actuator 12 by adhesive, weld or mechanical connection.

In the embodiment illustrate in FIG. 1, the first and second portions 34 and 36 preferably are integral, and a frangible or weakened section 42 is located between the first and second portions 34, 36 and extends circumferentially around the detachment actuator 12. The frangible section 42 is designed to break or fracture when torque, preferably applied by finger pressure to the wings 35, 37, is applied to either the second portion 36 or the first portion 34 of the detachment actuator 12 while the other of said portions 34, 36 is held in a stationary position. After the frangible section 42 has fractured, the second portion 36 is detached from the first portion 34 and can be moved in a proximal direction to separate the second portion 36 a distance from the first portion 34. For example, referring to FIG. 3, when torque is applied to the second portion 36 in the direction of arrow A and the first portion 34 is held in a stationary position, the frangible section 42 fractures, thereby detaching the second portion 36 from the first portion 34. In other words, the frangible section 42 is designed to fracture when there is relative rotation between the first and second portions 34, 36 of the detachment actuator 12.

The detachment actuator 12 can be made of polymeric and/or metallic materials. The detachment actuator 12 may be made out of any suitable material that will accommodate a frangible section and allow such section to fracture when torque is applied to the detachment actuator 12. Preferably, the frangible section 42 will fracture when torque is applied at a pressure that is able to be applied by a human hand, or by operation of so-called digital force. Alternatively, the torque may be applied by an instrument, which typically would be able to apply greater than digital force in a closely controlled manner. Furthermore, the strength of the frangible section, and thus the amount of torque required to fracture said section, can be varied by varying the length, thickness and type of material of the frangible section.

As shown in FIG. 4, after the second portion 36 of the detachment actuator 12 has been detached from the first portion 34, the second portion 36 can be separated from the first portion 34 by a distance in the proximal direction. When the second portion 36 is separated from the first portion 34, the control member 26, which is connected to the second portion 36, also moves proximally relative to the engagement member 20. In the illustrated detachment system for the medical device that is shown in the drawings, this proximal movement proceeds so that the distal end portion 33 of the control member 26 moves out of the opening 22 of the engagement member 20. Once the distal end portion 33 of the control member 26 is moved out of opening 22 of the engagement member 20, the unconstrained engagement member 20 is free to allow release of the medical device. FIG. 4 shows the engagement member 20 returned to its flat configuration, thereby releasing the medical device 30. This return can be due to a bias in the engagement member 20 or by a straightening-type of engagement with the medical device 30 as it separates from the detachment device.

According to one method of delivering the medical device 30, a tubular catheter (not shown) is fed into a body vessel until a distal end thereof is adjacent to a target location. Thereafter, the deployment system 10 and associated implantable medical device 30 are advanced through the catheter, using procedures and techniques known in the art, until the device 30 is itself generally adjacent to the target location. Alternatively, the deployment system 10 and associated device 30 may be pre-loaded in the catheter, with the combination being fed through a body vessel to a target location. Other methods of positioning the implantable medical device 30 generally adjacent to a target location may also be practiced without departing from the scope of the present invention.

To more accurately position the engaged device 30, radiopaque markers (not illustrated) may be attached to the carrier member 14 or the device 30 itself.

When the engaged device 30 has been properly positioned and oriented, torque is applied to the second portion 36 of the detachment actuator 12 while the first portion 34 is held in a stationary position to fracture the frangible section 42, thereby detaching the second portion 36 from the first portion 34, as illustrated in FIG. 3. Alternatively, torque could be applied to the first portion 34 while the second portion 36 is held stationary, or torque could be applied to one of said first and second portions 34, 36 in one direction and applied to the other of said portions in the opposite direction.

Referring to FIG. 4, the second portion 36 is then separated from the first portion 34 by moving the second portion 36 in a proximal direction away from the first portion 34. Movement of the second portion 36 away from the first portion 34 causes the control member 26 to move in a proximal direction and out of engagement with the engagement member 20. The engagement member 20 is allowed to return to its original substantially flat condition, or is moved to a release condition by engagement with another component of the system, thereby disengaging the aperture-containing end portion 32 of the implantable medical device 30 and deploying the medical device 30. The control member 26 may be provided with a radiopaque portion to provide visual feedback to indicate when the device 30 has been released.

When the implantable medical device 30 is disengaged from the engagement member 20, the deployment system 10 may be removed from the patient alone or in conjunction with the catheter.

As can be appreciated from the above description, the detachment actuator 12 provides a safety mechanism that will reduce the risk of premature release of the medical device.

Specifically, the medical device cannot be released from the deployment system until the frangible section of the detachment actuator is fractured.

FIGS. 5 and 6 illustrate an alternative embodiment of a detachment actuator according to the present invention that provides for a more controlled, incremental movement of the control member 26a during release of the medical device 30a.

In this embodiment, the deployment system 10a includes a detachment actuator 12a which is similar in many aspects to detachment actuator 12 of the previous embodiment except that detachment actuator 12a includes an angled frangible section 42a. When release of the medical device 30a is desired, torque is applied to the detachment actuator 12a in any of the manners described above, for example by applying torque to the wings 35a of the second portion 36a while holding the first portion 34a in a stationary position. Applying torque to the detachment actuator 12a causes the frangible section 42a to fracture so that the second portion 36a has an angled surface 44a at its distal end 48a and the first portion 34a includes a corresponding angled surface 46a at its proximal end 50a.

After the frangible section 42a has been fractured, the first and second portions 34a, 36a are rotated relative to each other, and the angled surfaces 44a, 46a function as cam surfaces that cause the second portion 36a to move proximally relative to the first portion 34a in a controlled, incremental fashion. In the illustrated embodiment, the second portion 36a will be the furthest away from the first portion 34a, when the second portion 36a is rotated 180 degrees relative to the first portion 34a. Additionally, the maximum proximal movement of the second portion 36a as a result of the cam surfaces 44a, 46a is controlled by the angle of the surfaces and the amount of relative rotational movement between the first and second portions 34a, 36a. For example, if greater proximal movement of the second portion 36a is desired, the frangible section 42a can be configured to result in cam surfaces of greater angles after when the frangible section 42a is fractured If more proximal movement is desired beyond that which is provided by the cam surfaces, the second portion 36a may be pulled in the proximal direction.

As illustrated in FIG. 6, movement of the second portion 36a of the detachment actuator 12a in the proximal direction causes the control member 26a to also move in the proximal direction so that the distal end portion 33a of the control member 26a disengages engagement element 20a, thereby releasing medical device 30a in a similar manner as described above Preferably, the angle of the cam surfaces 44a, 46a are such that the second portion 36a moves a distance that is sufficient to cause the control member 26a to come out of engagement with engagement member 20a.

Figure 9:
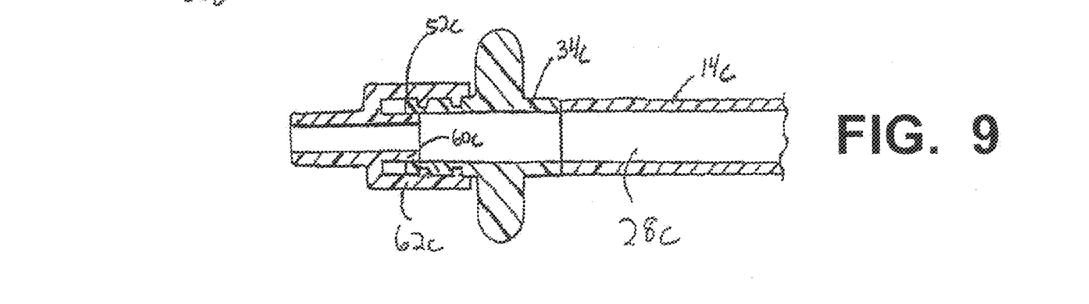
FIG. 9 is a cross-sectional view of the deployment device of FIG. 7 shown with the second portion of the detachment actuator and the control member removed, and a standard luer and luer lock connected to the first portion of the detachment actuator.

FIGS. 7-9 illustrate yet another embodiment of a detachment actuator in accordance with the present invention. As illustrated in FIGS. 7 and 8, the deployment system 10c includes a detachment actuator 12c. In this embodiment, the first and second portions 34c, 36c of the detachment actuator 12c are discrete elements which are attached to each other by a threaded engagement.

The proximal end portion 52c of the first portion 34c includes an outwardly threaded surface 54c, and the distal end portion 56c of the second portion 36c includes an inwardly threaded surface 58c that receives and threadably engages the proximal end portion 52c of the first portion 34c to secure the first portion 34c to the second portion 36c as illustrated in FIG. 7. In the illustrated embodiment, the proximal end portion 52c of the first portion 34c is configured to receive a standard luer and luer lock, and the distal end portion 56c of the second portion 36c has the same configuration as a standard luer lock. However, the threaded portions of the first and second portions 34c, 36c of the detachment actuator 12c can take on various forms depending on the desired configuration and use. It will also be understood that the threaded portions of the first and second portions 34c, 36c could be reversed in that the distal end portion of the second portion 36c could comprises the outwardly threaded portion and the proximal end of the first portion 34c could comprise the inwardly threaded portion.

To release the medical device 30c, torque is applied to the detachment actuator 12c using any of the methods described above, causing the second portion 36c of the detachment actuator 12c to unthread from the first portion 34c. As the second portion 36c is unthreaded from the first portion 34c, the second portion 36c moves in an axial direction away from the first portion 34c, causing the control member 26c to move in a proximal direction relative to the engagement member 20c. Movement of the control member 26c in the proximal direction causes the distal end portion 33c of the control member 26c to disengage engagement member 20c. The unconstrained engagement member 20c returns to its flattened condition, thereby releasing the medical device 30c as shown in FIG. 8.

Similar to the previous embodiment illustrated in FIGS. 4-6, the thread engagement between the first and second portions 34c, 36c results in a controllable smooth incremental movement of the control member 26c. Preferably, the size and length of the threading is such that the movement of the second portion 36c away from the first portion 34c caused by the unthreading is sufficient to move the distal end portion 33c of the control member 26c out of engagement with the engagement member 20c. However, if more movement is required or desired, the second portion 36c may be pulled in a proximal direction after it has become completely unthreaded and detached from the first portion 34c.

Referring to FIG. 9, in an alterative embodiment, the first portion 34c of the detachment actuator 12c and the carrier member 14c can be employed to deliver fluids, such as drugs or the like, to the patient after the medical device 30c has been deployed For example, as indicated above, the threaded surface located on the proximal end 52c of the first portion 34c can be configured to accept a standard male luer 60c and luer lock 62c. After the second portion 36c and the control member 20c have been removed from the system, a male luer 60c, being a part of a fluid delivery device, such as a syringe or I.V. system, may be threadably connected to the first portion 34c of the detachment actuator to deliver fluids through the lumen 28c of the carrier member 14c to the patient.

It will be seen from the preceding description that detachment actuators according to the present invention eliminate numerous problems associated with known devices. In particular, detachment actuators and associated methods of use according to the present invention ensure a controlled release of the implantable device to the target location and reduce the risk of a premature release of the medical device.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:
1. An actuator for use with an implantable medical device deployment system including a control member that controls the release of the implantable medical device upon movement of the control member, the actuator comprising:

a first portion, a second portion and a fracturable member located between the first and second portions, said first portion being adapted to be connected to the deployment system and said second portion being adapted to be connected to the control member; and said second portion being detachable from said first portion upon the application of torque to either said first portion or said second portion, thereby fracturing the fracturable member and allowing said second portion to be separated by a distance from said first portion to cause movement of the control member through an elongated carrier member to release the medical device.

2. The actuator of claim 1 in which the first and second portions are integral, and the fracturable member is associated with the first and second portions to detach the second portion from the first portion.

3. The actuator of claim 2 in which the fracturable member includes a frangible section between the first and second portions that is fractured to detach the second portion from the first portion.

4. The actuator of claim 3 in which the frangible section is at an angled relative to the first and second portions.

5. The actuator of claim 1 in which relative rotational movement between the first and second portions causes the first and second portions to separate by a distance.

6. The actuator of claim 5 in which the first and second portions are discrete portions that are threadably attached.

7. The actuator of claim 6 in which the second portion includes a threaded luer lock and the first portion is configured to engage the threaded luer lock.

8. The actuator of claim 5 in which the first and second portions include cam surfaces which cause the first and second portions to separate when the first and second portions are rotated relative to one another.

9. An actuator for use with an implantable medical device deployment system including a control member that controls the release of the implantable medical device upon movement the control member, the actuator comprising:

a first portion, a second portion and a fracturable member located between the first and second portions, wherein said first portion and said second portion are integral, said first portion being adapted to be connected to the deployment system and said second portion being adapted to be connected to the control member; and the fracturable member between the first and second portions such that said second portion is detachable from said first portion by fracturing said fracturable member by applying torque to the first portion or the second portion of the actuator, thereby allowing said second portion to be separated by a distance from said first portion to cause movement of the control member through an elongated carrier member to release the medical device, wherein the actuator is configured to be fractured by applying torque to the first portion or the second portion of the actuator.

10. The actuator of claim 9 in which the fracturable member is a frangible section between the first and second portions that is fractured to detach the second portion from the first portion.

11. The actuator of claim 10 in which the frangible section is at an angled relative to the first and second portions.

12. A deployment system for delivering an implantable medical device to a target location of a body vessel, comprising:

a generally elongated carrier member having a proximal end portion and a distal end portion;

an implantable medical device releasably attached to the distal end portion of the carrier member a control member whose movement through the elongated carrier member causes the release of the implantable medical device from the distal end portion of the carrier member;

an actuator including a first portion, a second portion and a fracturable member located between the first and second portions, said first portion of the actuator being connected to the carrier member and said second portion of the actuator being connected to the control member; and said second portion of the actuator being detachable from said first portion of the actuator upon the application of torque to either said first portion or said second portion of the actuator, thereby fracturing the fracturable member and allowing said second portion of the actuator to be separated by a distance from said first portion of the actuator to cause movement of the control member and release of the implantable medical device.

13. The deployment system of claim 12 in which the first and second portions of the actuator are integral and the actuator is fractured to detach the second portion from the first portion.

14. The deployment system of claim 13 in which the frangible section is at an angled relative to the first and second portions.

15. The deployment system of claim 13 in which the first and second portions are discrete portions that are threadably attached.

16. The deployment system of claim 15 in which the second portion includes a threaded luer lock and the first portion is configured to engage the threaded luer lock.

17. The deployment system of claim 16 further including a fluid system having a male luer and luer lock that engages the first portion of the actuator after the second portion has been detached from the first portion.

18. The deployment system of claim 12 in which the relative rotational movement between the first and second portions causes the first and second portions to separate by a distance.

19. The deployment system of claim 18 in which the first and second portions include cam surfaces which cause the first and second portions to separate when the first and second portions are rotated relative to one another.

20. The deployment system of claim 12 further including an engagement member associated with the distal end portion of the carrier member, the engagement member removably securing the implantable medical device to the distal end portion of the carrier member, and the control member engaging said engagement member such that movement of the control member causes release of the medical device from the engagement member.

21. The deployment system of claim 12 in which the control member comprises a wire.

22. A method of deploying an implantable medical device to a target location of a body vessel, comprising:

providing a generally elongated carrier member having a proximal end portion and a distal end portion, an implantable medical device releasably secured to the distal end portion of the carrier member, a control member whose movement through the elongated carrier member causes the release of the implantable medical device from the distal end portion of the carrier member, an actuator including a first portion, a second portion and a fracturable member located between the first and second portions, said first portion of the actuator being connected to the proximal end portion of the carrier member and said second portion of the actuator being connected to the control member;

positioning the implantable medical device generally adjacent to a target location within a body vessel;

detaching the second portion of the actuator from the first portion of the actuator by applying torque to either the first portion or second portion of the actuator thereby fracturing the fracturable member; and separating the second portion of the actuator from the first portion of the actuator, thereby causing movement of the control member and release of the medical device.

23. The method of claim 22 in which detaching the second portion of the actuator from the first portion of the actuator comprises unthreading the second portion of the actuator from the first portion of the actuator.

24. The method of claim 22 further including removing the second portion of the actuator and the control member, and delivering fluids through the carrier member.

25. The method of claim 24 wherein delivering fluids comprises attaching a fluid delivery system to the proximal end portion of the carrier member and pushing fluids through the carrier member.

* * * * *